US00PP32266P2

(12) United States Plant Patent
Gilham

(10) Patent No.: US PP32,266 P2
(45) Date of Patent: Oct. 6, 2020

(54) FLORIBUNDA ROSE PLANT NAMED 'PNKTER'

(50) Latin Name: ***Rosa* hybrid**
Varietal Denomination: PNKTER

(71) Applicants: John Charles Gray, Highfields (AU); Sylvia Elizabeth Gray, Highfields (AU)

(72) Inventor: Scott Alan Gilham, Sarasota, FL (US)

(73) Assignees: John Charles Gray, Highfields (AU); Sylvia Elizabeth Gray, Highfields (AU)

( * ) Notice: Subject to any disclaimer, the term of this patent is extended or adjusted under 35 U.S.C. 154(b) by 0 days.

(21) Appl. No.: 16/602,540

(22) Filed: Oct. 25, 2019

(51) Int. Cl.
*A01H 5/02* (2018.01)
*A01H 6/74* (2018.01)

(52) U.S. Cl.
USPC ..... Plt./148
CPC ..... *A01H 6/749* (2018.05)

(58) Field of Classification Search
USPC ..... Plt./148
CPC ..... A01H 5/0222
See application file for complete search history.

*Primary Examiner* — Kent L Bell
(74) *Attorney, Agent, or Firm* — Samuel R. McCoy, Jr.

(57) ABSTRACT

'PNKTER' is a new and distinct *Rosa* hybrid plant which is characterized by the combination of a bushy growth habit with an abundance of doubled-type pink flowers born on terminal corymbs, strongly perfumed flowers, very high resistance to blackspot and powdery mildew diseases, and the stability of these characteristics from generation to generation.

2 Drawing Sheets

Latin name of genus and species: The Latin name of the genus and species of the novel variety disclosed herein is *Rosa* hybrid.

Variety denomination: The inventive variety of *Rosa* disclosed herein has been given the variety denomination 'PNKTER'.

BACKGROUND OF THE INVENTION

Parentage: 'PNKTER' originated as a naturally occurring, branch mutation of *Rosa* hybrid 'GRAppl' (U.S. Plant Pat. No. 26,364). On Jun. 16, 2018, the inventor discovered the mutation at a commercial greenhouse operation in Sarasota, Fla., growing amongst a crop of *Rosa* hybrid 'GRAppl'. The mutated branch was noted for its pink flower, compared to the purple flowers of the parent. Cuttings were taken from the mutated branch, rooted, and then grown out for further evaluation in order to confirm the distinctness and stability of the characteristics first observed. Upon confirmation of distinctness and stability, 'PNKTER' was selected for commercialization.

Asexual Reproduction: Asexual propagation of 'PNKTER', by way of softwood stem cuttings, was first performed in the June of 2018 at a commercial greenhouse in Sarasota, Fla. Through at least 20 subsequent generations, the unique features of this cultivar have proven to be stable and true to type.

SUMMARY OF THE INVENTION

The following characteristics have been repeatedly observed and represent the distinguishing characteristics of the new *Rosa* cultivar 'PNKTER'. These traits, in combination, distinguish 'PNKTER' as a new and distinct cultivar.

1. *Rosa* 'PNKTER' exhibits a freely-branching, upright to semi-upright growth habit; and 2. *Rosa* 'PNKTER' exhibits excellent resistance to rose black spot disease (*Diplocarpon rosae*) and powdery mildew (*Podosphaera pannosa*); and
3. *Rosa* 'PNKTER' exhibits recurrent to nearly continuous flowering with flowers borne on terminal corymbs, usually with three to four flowers per corymb; and
5. *Rosa* 'PNKTER' exhibits pink doubled-type flowers; and
6. *Rosa* 'PNKTER' exhibits flowers with a strong sweet to traditional rose fragrance.

DETAILED BOTANICAL DESCRIPTION

Figure 1:
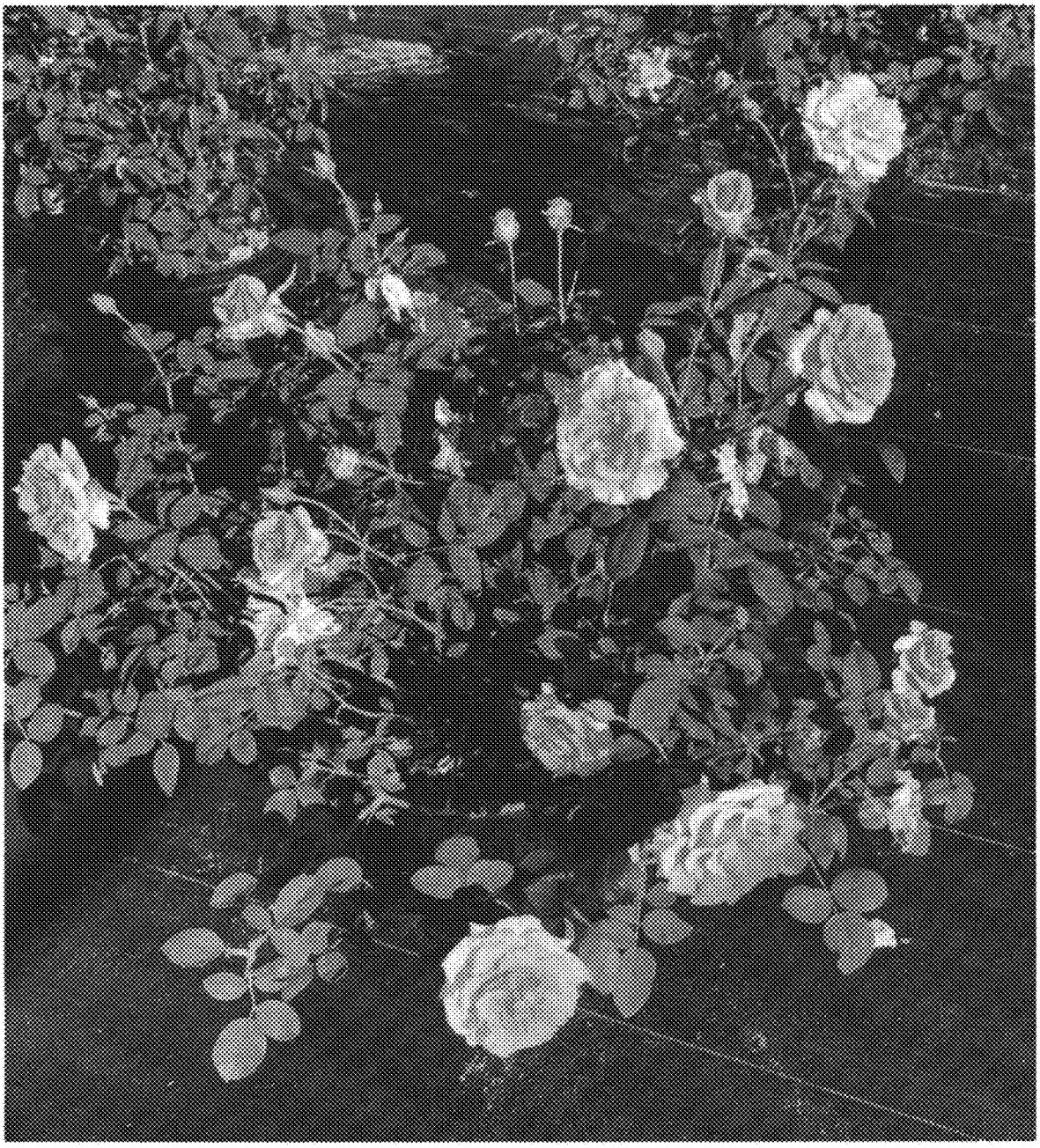
FIG. 1 illustrates, as nearly true as it is reasonably possible to make the same in color photographs of this type, an exemplary 6 month old 'PNKTER' plant grown outdoors at a commercial nursery in Sarasota, Fla.
Figure 2:
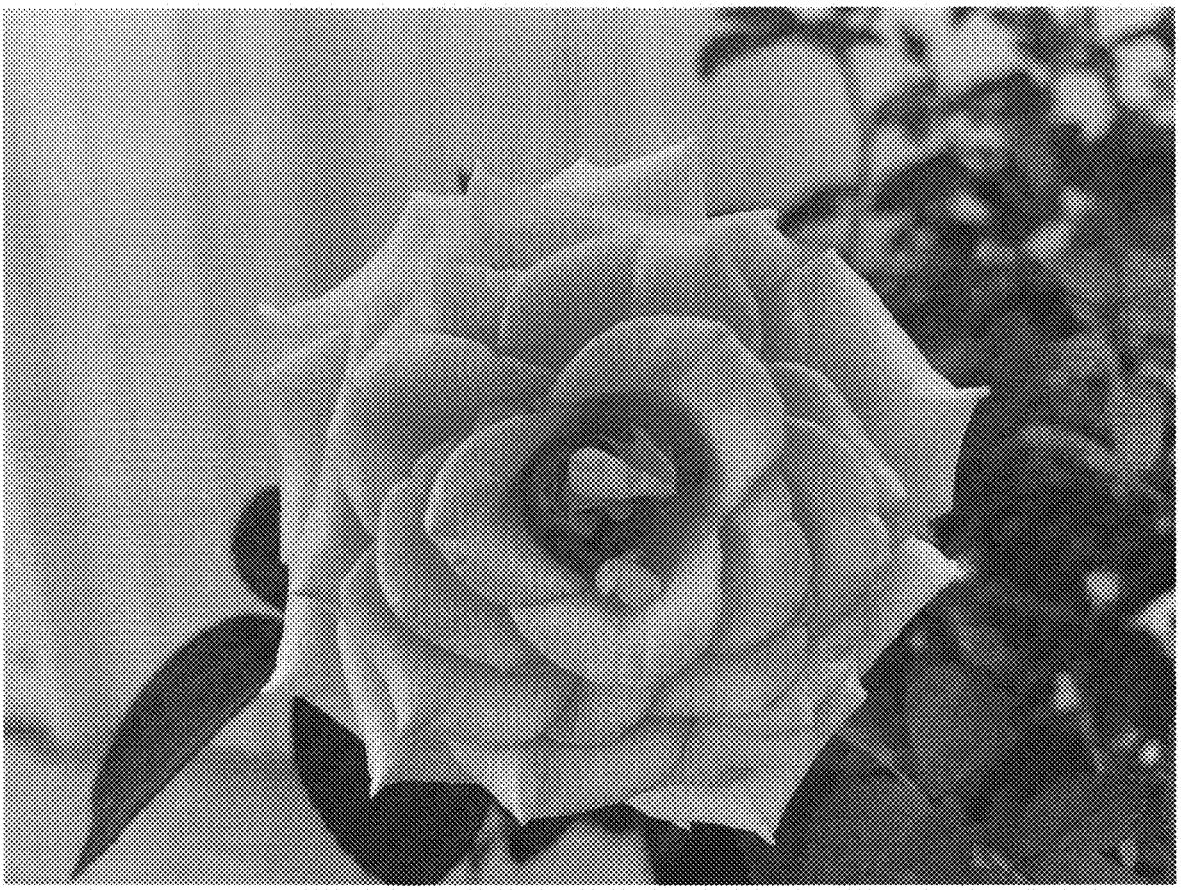
FIG. 2 illustrates, as nearly true as it is reasonably possible to make the same in color photographs of this type, the typical flower of 'PNKTER'.

The following is a detailed botanical description of a new and distinct *Rosa* hybrid plant known as 'PNKTER'. Plant observations were made on a container-grown plant produced outdoors in Sarasota, Fla. Unless indicated otherwise, the descriptions disclosed herein are based upon observations made of a six month old 'PNKTER' plant, grown in a three gallon nursery container. The plant was grown in full sun, provided regular manual irrigation, and fertilized approximately every three months with a slow-release granular fertilizer. Fungicide and insecticides were applied in both preventative and curative applications, as needed. Observation data were recorded in the September of 2019.

Those skilled in the art will appreciate that certain characteristics will vary with older or, conversely, with younger plants. 'PNKTER' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 1986 edition except where common terms of color are used.

A botanical description of 'PNKTER' and comparisons with the parent and most similar commercial variety known to the inventor are provided below.

General plant description:

*Growth habit*.—Upright to semi-upright.

*Growth rate*.—Approximately 6 months to reach 60 cm.

*Dimensions*.—50 cm tall and 70 cm wide, as observed. Mature plants can reach 120 cm tall and 100 cm wide.

*Environmental tolerance*.—Very good heat tolerance; cold hardy to USDA Zone 5.

*Disease resistance*.—Excellent resistance to powdery mildew (*Podosphaera pannosa*) and blackspot (*Diplocarpon rosae*).

*Propagation*.—Technique — Softwood stem cuttings. Time to initiate roots — About 13 days at approximately 21 degrees Celsius at root zone and 18 degrees Celsius ambient temperature. Time to produce a rooted cutting — About 25 days at approximately 21 degrees Celsius at root zone and 18 degrees Celsius ambient temperature.

Root system:

*Type*.—Moderately fibrous root system.

*Branching*.—Moderately branched.

*Density*.—Moderately dense.

*Distribution*.—Roots distributed evenly throughout the soil profile, from shallow to deep.

*Texture*.—Smooth; lacking root hairs.

Stems:

*Branching habit*.—Irregular branching from mature branches, breaking first from the uppermost buds near the apex of each shoot.

*Quantity*.—Numerous.

*General dimensions*.—Approximately 35 cm long; 1.5 cm in diameter near the base and tapering to 1.0 cm.

*Immature branches*.—Length — Longest observed is 30 cm; 17 cm on average. Diameter — Approximately 0.3 cm. Texture and pubescence — Smooth, glabrous, and very slightly pruinose; prickles present. Color — Yellow-green, nearest to in between RHS 144A and 146D. Prickles — Density — Sparse to moderate. Dimensions — 3.5 mm long and 1.25 mm wide at the base. Color — Yellow-green, nearest to RHS 151A. Shape — Narrowly deltoid. Texture — Smooth.

*Mature branches*.—Diameter — Approximately 1.0 cm, after one year. Texture and pubescence — Glabrous and fissured; prickles present. Color — Nearest to a mixture of green, RHS 143C, and yellow-green, RHS 144A. Prickles — Density — Sparse to moderate. Dimensions — 5.5 mm long and 1.5 mm wide at the base. Color — Nearest to yellow-green, RHS 145C, and heavily suffused with greyed-orange, RHS 165D, with age. Shape — Deltoid; recurved. Texture — Smooth.

Leaves:

*Arrangement*.—Imparipinnate compound leaves.

*Attachment*.—Petiolate.

*Dimensions*.—95 mm long and 62.5 mm wide.

*Abundance*.—Very abundant.

*Petiole*.—Length — Average 20 mm. Diameter — Average 2.0 mm. Petiole color, adaxial surface — Yellow-green, nearest to RHS 146C, and suffused with greyed-red, RHS 178A. Petiole color, abaxial surface — Yellow-green, nearest to RHS 146C. Texture and luster, adaxial surface — Glabrous; matte. Texture and luster, abaxial surface — Glabrous; matte. Prickles — Density — Sparse on the abaxial surface; none present on the adaxial surface. Dimensions — 3.5 mm long and 1.25 mm wide at the base. Color — Yellow-green, nearest to RHS 151A. Shape — Narrowly deltoid. Texture — Smooth. Stipitate glands — Absent.

*Stipules*.—Size — 11 mm long and 6.0 mm wide. Stipule color, adaxial surface — Yellow-green, nearest to RHS 147A. Stipule color, abaxial surface — Yellow-green, nearest to RHS 147B. Stipitate glands — Only present at margins. Margins — Cilliate. Texture, adaxial surface — Glabrous; lightly bullate. Texture, abaxial surface — Glabrous; lightly bullate. Apex — Acuminate. Base — Winged.

*Rachis*.—Length — Average 15 mm. Diameter — Average 1.5 mm. Color, adaxial surface — Yellow-green, nearest to RHS 146C, and heavily suffused with greyed-red, RHS 178A. Color, abaxial surface — Yellow-green, nearest to RHS 146C. Stipitate glands — Sparse. Texture and luster, adaxial surface — Glabrous; matte. Texture and luster, abaxial surface — Glabrous; matte. Prickles — Density — Sparse on the abaxial surface; none present on the adaxial surface. Dimensions — 3.5 mm long and 1.25 mm wide at the base. Color — Yellow-green, nearest to RHS 151A. Shape — Narrowly deltoid. Texture — Smooth.

*Leaflets*.—Quantity — Some leaves with 5 leaflets; others with 7 leaflets. Dimensions — Average size of the terminal leaflet is 42 mm long and 31 mm wide. Shape — Ovate. Apex — Acuminate. Base — Obtuse. Margins — Serrated; slight undulation is occasionally present. Texture, adaxial surface — Glabrous and slightly rugose. Texture, abaxial surface — Glabrous and slightly rugose. Luster, adaxial surface — Matte to semi-glossy. Luster, abaxial surface — Matte. Color — Juvenile leaflet, adaxial surface — Yellow-green, RHS 144A, and margined greyed-red, RHS 178B. Juvenile leaflet, abaxial surface — Yellow-green, RHS 144B, and moderately suffused and margined greyed-red, RHS 178B. Mature leaflet, adaxial surface — Nearest to a mixture of green, RHS 137B, and yellow-green, RHS 147A. Mature leaflet, abaxial surface — Yellow-green, nearest to RHS 147C. Venation — Pattern — Reticulate. Color, adaxial surface — Yellow-green, nearest to in between RHS 144A and 144B. Color, abaxial surface — Yellow-green, nearest to RHS 146C. Petiolule — Dimensions — 2.0 mm long and 1.0 mm in diameter. Petiolule color, adaxial surface — Yellow-green, nearest to RHS 146C, and suffused with greyed-red, RHS 178A. Petiolule color, abaxial surface — Yellow-green, nearest to RHS 146C. Prickles — Absent. Stipitate Glands — Absent. Texture, adaxial and abaxial surfaces — Smooth; glabrous.

Inflorescence:

*Inflorescence type*.—Terminal corymbs.

*Blooming habit*.—Recurrent to nearly continuous flowering; blooming nearly year-long in Sarasota, Fla.

*Time to flower*.—4 to 6 weeks for a maturing stem to produce flowers.

*Quantity of flowers*.—Generally 3 to 4 pedicillate flowers per corymb.

*Size*.—Corymbs are typically 80 mm tall and 80 mm wide.

*Peduncle*.—Surface — Lacking stipitate glands. Length — 55 mm. Diameter — 2.0 mm. Color — Yellow-green, nearest to a combination of RHS 144C and 145B. Strength — Strong. Texture — Glabrous; sparsely to moderately covered with stipitate glands.

Bud:

*Bud form*.—Pointed ovoid.

*Size*.—Upon opening, 17 mm in length and 11 mm diameter at its widest point.

*Texture and luster*.—Smooth, glabrous, and matte.

*Color, prior to bud-break*.—Yellow-green, nearest to RHS 144A, and lightly suffused with greyed-red, RHS 182B.

Flower:

*Pedicel*.—Length — 30 mm. Diameter — 2.0 mm. Color — Yellow-green, nearest to RHS 144C, and moderately suffused with greyed-red, RHS 182B. Strength — Strong. Texture — Moderately covered with stipitate glands.

*Calyx*.—General — Comprised of five heavily-reflexed polysepalous sepals, with weak foliaceous appendages present on three of the five sepals. Diameter of calyx — 11 mm, at anthesis. Sepals — Color, interior surface — Yellow-green, nearest to a mixture of RHS 146B and 146C. Color, exterior surface — Yellow-green, nearest to RHS 146B. Dimensions — 21 mm long and 5.0 mm wide at the base. Apex — Acuminate. Base — Flat at union with receptacle. Texture, interior surface — Heavily felted. Texture, exterior surface — Lightly felted. Margins — Ciliate. Stipitate glands — Present at the margins; moderately dense.

*Corolla*.—General shape of corolla — Rounded to somewhat star-shaped. Shape of corolla when viewed from the side — Upon opening, upper portion — Flattened convex. Upon opening, lower portion — Concave. Open flower, upper portion — Flat. Open flower, lower portion — Concave. Aspect — Flowers held upright to outward. Dimensions — 90 mm and the average flower height is 50 mm. Fragrance — Strong; a mixture of sweet perfume and traditional rose fragrance. Duration — On the plant approximately 6 days. Senesced petals drop away cleanly. Petals — Petal arrangement — Very doubled, tightly whorled petal arrangement. Petal count — 40 petals. Petal reflex — Moderately reflexed. Petal margin — Entire; lightly undulated. Petal shape — Rounded. Apex — Rounded. Base — Obtuse. Dimensions — Approximately 35 mm long and 32 mm wide. Texture and luster, inner surface — Smooth, soft and matte. Texture and luster, outer surface — Smooth, soft and matte. Petal color, upon opening — Outer surface — Red-purple, nearest to a mixture of RHS 58D and 62A. Inner surface — Red-purple, nearest to a mixture of RHS 58D and 62A. Basal petal spots, upon opening — Color, outer surface — Yellow, nearest to RHS 5D. Color, inner surface — Yellow, nearest to RHS 5D. Petal color, at anthesis — Outer surface — Red-purple, RHS 63D, and suffused with a darker shade of red-purple, nearest to a combination of RHS 63C and 64D. Inner surface — Red-purple, RHS 63D, and suffused with a darker shade of red-purple, nearest to a combination of RHS 63C and 64D. Basal petal spots, after opening — Color, outer surface — Yellow, nearest to RHS 11D. Color, inner surface — Yellow, nearest to RHS 11D. Petal color, when fading — Outer surface — Red-purple, RHS 62D. Inner surface — Red-purple, RHS 62D.

Reproductive organs:

*Stamens*.—Quantity — Approximately 50, on average, and regularly arranged around the styles. Anthers — Shape — Globose to oblong, with two anther sacs. Dimensions — 1.25 mm long and 0.75 mm wide. Color — Greyed-orange, nearest to a mixture of RHS 167A and 169C. Pollen — Abundant. Pollen Color — Yellow-orange, RHS 23A. Filaments — Color — Yellow-green, RHS 150D. Dimensions — Varying from 8 to 11 mm long and 0.5 to 0.75 mm in diameter.

*Pistils*.—Quantity — Approximately 35 to 40. Overall length — 7 to 8 mm. Stigmas — Shape — Rounded. Position — Slightly inferior to anthers. Color — Yellow-orange, RHS 18B. Styles — Dimensions — 4.0 mm long and 0.75 mm in diameter. Color — Yellow-orange, RHS 18C, and becoming heavily suffused with red, RHS 43B, towards the stigma.

*Ovary*.—Position — Superior. Dimensions — 4.5 mm long and 3.0 mm in diameter. Color — Yellow-green, RHS 150C.

*Receptacle*.—Shape — Pitcher-shaped. Dimensions — Approximately 6.0 mm high and 6.0 mm wide. Surface — Glabrous and slightly glaucous. Color — Yellow-green, nearest to a mixture of RHS 145A and 145B. Texture — Smooth.

Hips and seeds: Not observed.

Comparisons With the Parent

Plants of the new cultivar 'PNKTER' may be distinguished from its parent, *Rosa* hybrid 'GRAppl' (U.S. Plant Pat. No. 26,364), by the characteristics described in

TABLE 1

| Characteristic | 'PNKTER' | 'GRAppl' |
|---|---|---|
| Growth habit. | More freely branching than 'GRAppl'. | Less freely branching than 'PNKTER'. |
| Fragrance. | A mixture of traditional rose and sweet perfume. | Traditional rose. |
| General coloration of the flower. | Pink (i.e. a lighter shade of red-purple) | Purple (i.e. a darker shade o fred-purple). |

Comparison With the Closest Known Commercial Comparator

Plants of the new cultivar 'PNKTER' may be distinguished from the most similar known commercial comparator, *Rosa* sp. 'GRAcha' (U.S. patent application Ser. No. 16/350,970), by the characteristics described in Table 2.

TABLE 2

| Characteristic | 'PNKTER' | 'GRAcha' |
|---|---|---|
| Clinginess of flower petals. | Self-cleaning. | Petals are clinging. |
| General coloration of the flower, at anthesis. | Lighter pink (i.e. a lighter shade of red-purple). | Darker pink (i.e. a darker shade of red-purple). |
| Flower fragrance. | A mixture of sweet perfume and traditional rose fragrance. | Traditional rose scent. |

That which is claimed:

1. A new and distinct variety of rose plant named 'PNKTER', as described and illustrated herein.

* * * * *